(12) United States Patent
Parks et al.

(10) Patent No.: US 8,221,369 B2
(45) Date of Patent: *Jul. 17, 2012

(54) FLUID VOIDING APPARATUS

(75) Inventors: Mark Parks, Minneapolis, MN (US); James C. Block, Maple Plain, MN (US)

(73) Assignee: FemMed, Inc., Minnetonka, MN (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/689,801

(22) Filed: Jan. 19, 2010

(65) Prior Publication Data

US 2010/0121289 A1 May 13, 2010

Related U.S. Application Data

(63) Continuation of application No. 10/839,723, filed on May 4, 2004, now Pat. No. 7,682,347, which is a continuation-in-part of application No. 10/453,316, filed on Jun. 3, 2003.

(60) Provisional application No. 60/390,685, filed on Jun. 18, 2002.

(51) Int. Cl.
*A61F 5/44* (2006.01)

(52) U.S. Cl. ........ 604/355; 604/540; 604/544; 604/327; 604/328; 604/329; 604/330; 4/144.1; 4/144.2; 4/144.3; 206/363; 206/438; 206/570; 206/581; 206/210

(58) Field of Classification Search .................. 604/330, 604/335, 355
See application file for complete search history.

(56) References Cited

U.S. PATENT DOCUMENTS

| | | | |
|---|---|---|---|
| 190,244 A | 5/1877 | Olmstead |
| 618,624 A | 1/1899 | Stanek et al. |
| 3,473,172 A | 10/1969 | Friedman et al. |
| 3,522,808 A | 8/1970 | Worcester |
| 4,202,058 A | 5/1980 | Anderson |
| 4,484,917 A | 11/1984 | Blackmon |
| 4,568,339 A | 2/1986 | Steer |
| 4,771,484 A | 9/1988 | Mozell |
| 4,795,449 A | 1/1989 | Schneider et al. |
| 4,822,347 A | 4/1989 | MacDougall |
| 4,911,698 A | 3/1990 | Wapner |
| 4,917,238 A | 4/1990 | Schumacher |
| 4,936,823 A | 6/1990 | Colvin et al. |

(Continued)

FOREIGN PATENT DOCUMENTS

CN 1420750 A 5/2003

(Continued)

OTHER PUBLICATIONS

Form PCT/IB/326 from the corresponding PCT application, PCT/US2005/015491, 2005.

(Continued)

*Primary Examiner* — Tatyana Zalukaeva
*Assistant Examiner* — Ilya Treyger
(74) *Attorney, Agent, or Firm* — Hamre, Schumann, Mueller & Larson, P.C.

(57) ABSTRACT

An extra-labia urine voiding apparatus including a container sized and shaped to externally cover a vulval region of a female anatomy. The container has an open side and defines a reservoir that is adapted for receiving urine. The container also includes a surface disposed at a top of the container adapted to face and generally surround a periphery of the vulval region. The voiding apparatus also includes a conduit in fluid communication with the reservoir of the container and adapted for draining urine from the reservoir.

5 Claims, 7 Drawing Sheets

U.S. PATENT DOCUMENTS

| | | | |
|---|---|---|---|
| 5,091,998 | A | 3/1992 | Witzke |
| 5,147,301 | A | 9/1992 | Ruvio |
| 5,295,983 | A | 3/1994 | Kubo |
| 5,329,644 | A | 7/1994 | Scott |
| 5,457,823 | A | 10/1995 | Mojena |
| 5,571,095 | A | 11/1996 | Lu |
| D379,225 | S | 5/1997 | Canahuate et al. |
| 5,632,736 | A | 5/1997 | Block |
| 5,662,630 | A | 9/1997 | Raynie |
| 5,742,948 | A | 4/1998 | Cicio |
| 5,893,176 | A | 4/1999 | Magiera et al. |
| 5,894,608 | A | 4/1999 | Birbara |
| 5,931,304 | A | 8/1999 | Hammond |
| 6,041,448 | A | 3/2000 | Rempe et al. |
| 6,299,606 | B1 | 10/2001 | Young |
| 6,342,049 | B1 | 1/2002 | Nichols |
| 6,692,480 | B1 | 2/2004 | Bush |
| 6,740,066 | B2 | 5/2004 | Wolff et al. |
| 7,181,781 | B1 | 2/2007 | Trabold et al. |
| 2002/0157972 | A1 | 10/2002 | Gallo et al. |
| 2003/0149408 | A1 | 8/2003 | Levinson |

FOREIGN PATENT DOCUMENTS

| | | |
|---|---|---|
| GB | 2 090 144 | 7/1982 |
| WO | WO 98/43563 | 10/1998 |
| WO | WO 99/47760 | 9/1999 |
| WO | WO 03/105735 | 12/2003 |

OTHER PUBLICATIONS

Form PCT/IB/373 from the corresponding PCT application, PCT/US2005/015491, 2005.

Form PCT/ISA/237 from the corresponding PCT application, PCT/US2005/015491, 2005.

Chinese Office Action dated Apr. 4, 2008 and English translation of Office Action.

Int'l Search Report for WO 03/105735 AI. Parks et al.. Dec. 24, 2003. WIPO, A61F 5/455.

Encarta World Dictionary [North American Edition] 2007 Microsoft Corporation (http://encarta.msn.com/dictionary_1861698780/linear.html).

FLUID VOIDING APPARATUS

CROSS REFERENCE TO RELATED APPLICATIONS

This application is a Continuation of Ser. No. 10/839,723, filed May 4, 2004, which is a Continuation-in-Part of Ser. No. 10/453,316, filed Jun. 3, 2003, which claims priority to Provisional Application Ser. No. 60/390,685, filed Jun. 18, 2002.

FIELD OF THE INVENTION

The present invention relates generally to fluid voiding apparatuses. More particularly, the present invention relates to extra-labia fluid voiding apparatuses.

BACKGROUND OF THE INVENTION

The prior art discloses a variety of sanitary devices that are designed to allow females to void urine while standing up in order to avoid non-hygienic contact with toilet facilities. Such devices often include substantially rigid funnel structures adapted to cover the vulval region of a female anatomy. However, such substantially rigid funnel structures are typically bulky, not readily disposable, and require a user to hold the funnel structure against the body during urination in order to maintain a fluid tight seal thereby increasing the possibility of misdirecting the urine from the end of the funnel. Further, a user of such devices can experience uncomfortable side effects from urine splashing back at the user off the sidewall of the funnel structure, which may also lead to leakage out of the device, particularly where the seal is intended between the user and the device.

U.S. Pat. No. 4,568,339 discloses a female incontinence device including a generally funnel shaped receiving member that defines a groove into which an adhesive paste is disposed to provide a seal to prevent urine leakage. The device can be reused by replacing the adhesive paste each time the device is used.

U.S. Pat. Nos. 4,484,917; 4,795,449; and 4,822,347 each disclose female incontinence devices having inter-labia adhesive sealing structures. Such incontinence devices are typically designed as catheters for long term use.

U.S. Pat. No. 5,632,736 to Block discloses an extra-labia urine voiding apparatus including a container sized and shaped to externally cover a vulval region of a female anatomy. The container defines a reservoir and includes an open side that is adapted for receiving urine into the reservoir. The container also includes a flange having a substantially planar surface adapted to face and generally surround a periphery of the vulval region. An extra-labia sealing structure is affixed to the planar surface of the flange. The sealing structure includes a pressure sensitive adhesive adapted to provide a generally fluid tight primary adhesive seal between the container and external tissue generally surrounding the vulval region. The voiding apparatus also includes a conduit adapted for draining urine from the reservoir.

Although these devices may be suitable for their intended uses, improvements may still be made in providing a fluid voiding apparatus that prevents uncomfortable splash back at a user, while maintaining a fluid tight seal between the device and the user to prevent leakage. A fluid voiding apparatus is needed that provides optimum convenience for use and transport, and is cost effective for manufacture.

SUMMARY OF THE INVENTION

In accordance with the present invention, improvements upon existing female fluid voiding devices are made by providing a fluid voiding apparatus having a blocking mechanism that is capable of preventing fluid voided from a user's body from coming back into contact with the user.

The present invention is directed to an extra-labia fluid voiding apparatus that includes a container adapted to cover a vulval region of a female, and defines an open side in fluid communication with a reservoir that resides within the container and is adapted to receive fluid. The open side of the container defines a substantially planar surface connected to the container about a perimeter of the open side. In one embodiment, a sealing structure may be affixed to the planar surface. The planar surface may for example be adapted for providing an adhesive seal between the container and external tissue generally surrounding the vulval region. A blocking mechanism may be connected proximate the open side of the container, and is capable of preventing urine from escaping out of the open side of the fluid voiding apparatus and contacting a user of the apparatus. The container may include a conduit that is in fluid communication with the reservoir and is adapted for draining urine from the reservoir.

In one embodiment, the blocking mechanism includes a wall connected to the container and faces the reservoir. The wall is disposed proximate the open side of the container about a perimeter of the reservoir and extends a distance inward from the perimeter of the reservoir. The wall includes a blocking surface thereon, in which the blocking surface provides a front that counters urine voided from a user's body from escaping through the open side of the container and coming back into contact with the user.

In one embodiment, the blocking mechanism defines an overlap covering a portion of the reservoir.

In one embodiment, the blocking mechanism is directly opposite from the planar surface. Preferably, the blocking mechanism extends inward from the perimeter of the reservoir toward the opening of the open side.

In one embodiment, the blocking mechanism is substantially parallel with the open side and planar surface of the container.

In one embodiment, the extra-labia sealing structure and the blocking mechanism together prevent leakage of urine voided from a user's body out of the open side of the container.

In another embodiment, urine voiding apparatuses constructed in accordance with the principles of the present invention can be incorporated within compact urine voiding kits that include a moist antibacterial towelette or an absorbent material adapted for wiping the vulval region, a disposal bag, and a packaging structure for containing the urine voiding apparatus, the disposal bag and the absorbent material. Preferably, such a urine voiding kit can be easily carried, for instance, in a purse, daypack, or travel bag, while taking up a minimum amount of space.

In one embodiment, the present invention provides an efficient urine voiding apparatus for use by females that is light weight and compact so that it can be conveniently carried while occupying a minimum amount of space, such as in a purse. Another embodiment of the a urine voiding apparatus prevents uncomfortable splash back of urine at the user when the apparatus is being used during urination. Another embodiment of the present invention provides a urine voiding apparatus that is usable while disturbing a minimum amount of garb by the user. A further embodiment of the present invention provides a urine voiding apparatus for females that is sanitary and readily disposable after use. Also, embodiments of the present invention provide a urine voiding apparatus that maintains a hands-free seal thereby reducing the possibility of soiling clothing through the misdirection of urine.

A variety of additional advantages and objects of the invention will be set forth in part in the description which follows, and in part will be obvious from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

Referring now to the drawings in which like reference numbers represent corresponding parts throughout.

DETAILED DESCRIPTION OF THE INVENTION

Figure 1:
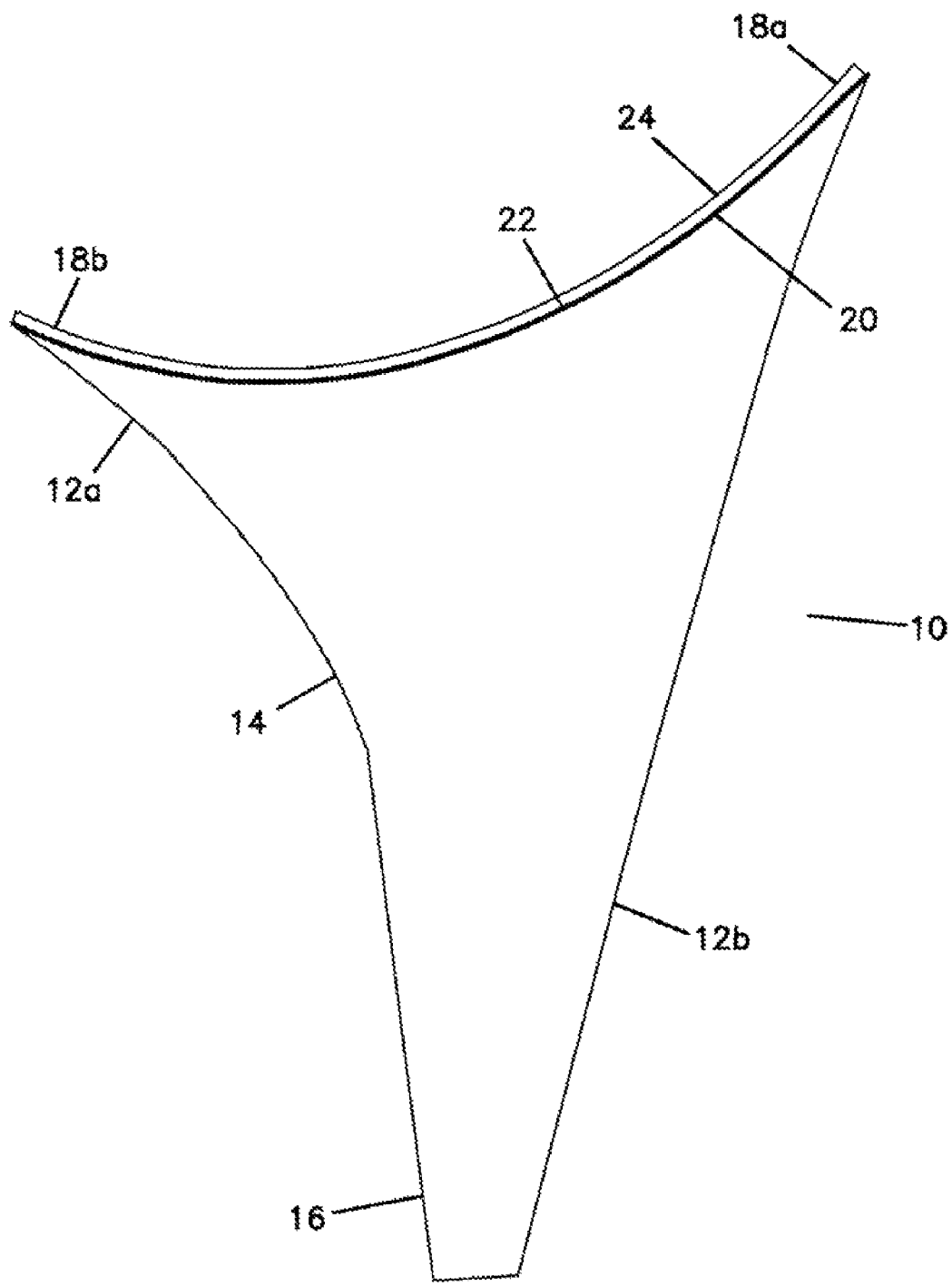
FIG. 1 represents an elevational side plan view of one embodiment of a urine voiding apparatus in accordance with the principles of the present invention.

In the following description of the illustrated embodiments, reference is made to the accompanying drawings that form a part hereof, and in which is shown by way of illustration of the embodiments in which the invention may be practiced. It is to be understood that other embodiments may be utilized as structural changes may be made without departing from the spirit and scope of the present invention.

FIGS. 1-4 show one embodiment of a urine voiding apparatus 10 constructed in accordance with the principles of the present invention. The urine voiding apparatus 10 includes a container 14 having top 12a and bottom 12b portions. The top 12a is sized and shaped to cover a vulval region of a female anatomy. The container 14 defines a reservoir 50 between the top 12a and bottom 12b adapted for receiving urine, where the reservoir 50 is in fluid communication with an open side 13 disposed at the top 12a of the container 14. The open side 13 allows urine discharged from a user's urethral orifice to be received into the reservoir 50.

Preferably, the urine voiding apparatus 10 includes a conduit 16 adapted for draining urine from the container 14 and reservoir 50. More preferably, the conduit 16 is integrally formed with the container 14 and is disposed proximate the bottom 12b of the container 14. An opening 52 resides at the bottom 12b of the container 14 enabling urine to be drained through the conduit 16 and out of the urine voiding apparatus 10.

A planar surface 20 is connected to the top 12a of the container 14 and extends generally about a perimeter of the open side 13 defined by the container 14. In one embodiment, an extra-labia sealing structure such as a pressure sensitive adhesive 22 is connected to the container 14 and is disposed on the planar surface 20. The extra-labia sealing structure extends generally around the perimeter of the open side 13. The pressure sensitive adhesive 22 is adapted for forming a generally fluid tight seal around a periphery of a user's vulval region, and prevents urine from leaking between the container 14 and a user's body. Optionally, a raised ridge 28, substantially resembling a rib-like structure or protrusion, is may be disposed proximate the top 12a of the container 14 on the planar surface 20 and about the perimeter of the outer surface of the container 14. The raised ridge 28 is adjacent the pressure sensitive adhesive 22. The raised ridge 28 assists in preventing leakage from the urine voiding apparatus 10 when the apparatus is supported against the periphery of a user's vulval region during use. It will be appreciated that a raised ridge resembling raised ridge 28 could also be included on the planar surface 20 at an inner perimeter of the planar surface 20. The pressure sensitive adhesive 22 also provides a structure such that use of the urine voiding apparatus may be hands free. It will be appreciated a pressure sensitive adhesive may not be employed, and a user may simply fit and press the planar surface 20 to the periphery of the vulval region as necessary to manually hold the urine voiding device 10 in place to provide a suitable seal.

Figure 2:
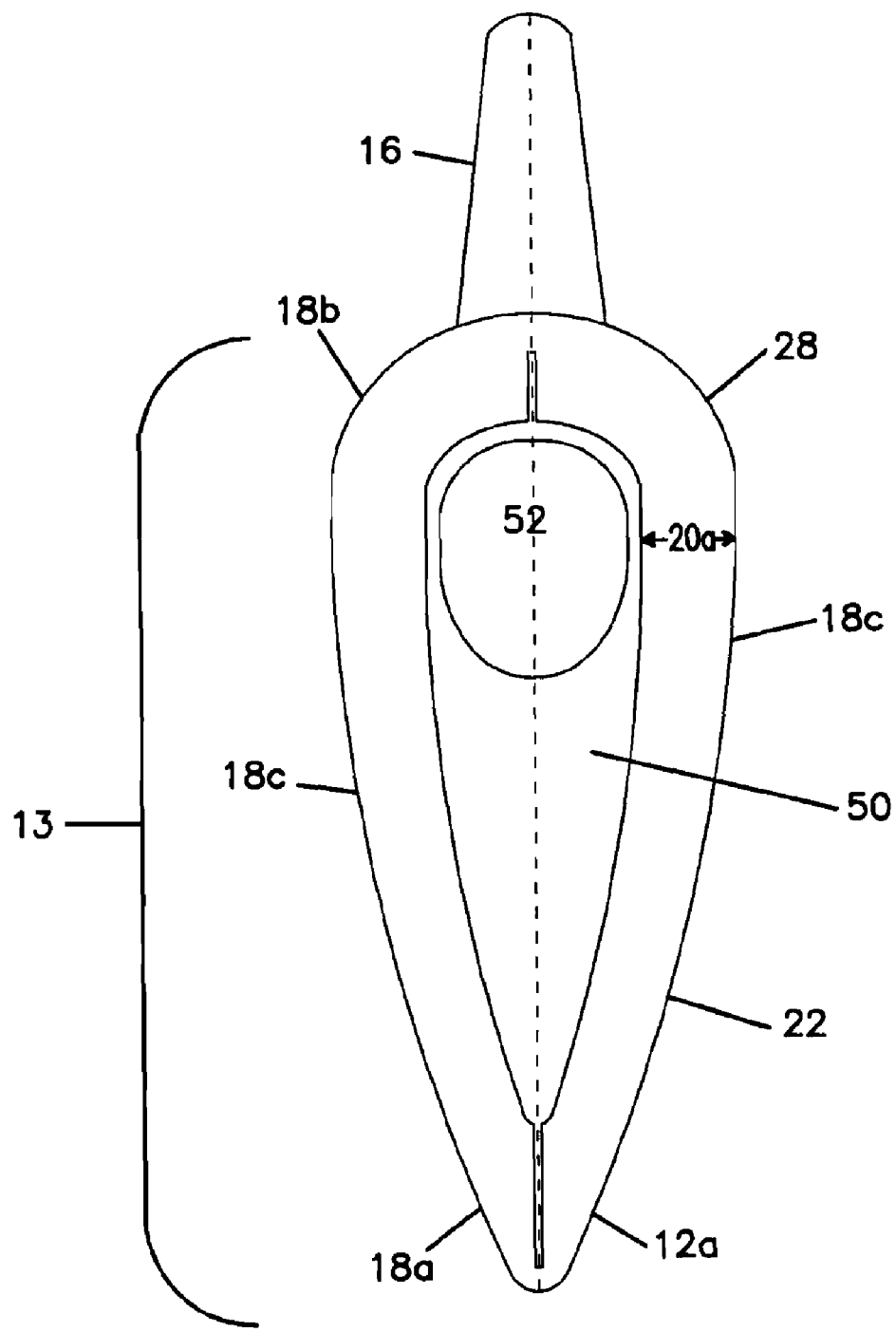
FIG. 2 represents an elevational top plan view of the urine voiding apparatus of FIG. 1.

As above, the container 14 includes the top 12a being sized and shaped to cover a vulval region of a female anatomy. As best shown in FIG. 2, the container 14 of the urine voiding apparatus 10 has a generally oval planform that defines the open side 13 and the reservoir 50 adapted for receiving urine. It will be appreciated that the planform of the container 14 also may be other shapes adaptable for covering the vulval region of a female anatomy. For example such shapes include, but are not limited to a triangular shape or hourglass shape.

Preferably, the top 12a is arranged and constructed in a curved configuration as best shown in FIG. 1, such that the top 12a is concave toward the reservoir 50. It will be appreciated that the degree of curvature of the top 12a may vary as needed. The container 14 includes a superior end 18b adapted to align generally with the mons Veneris of the female anatomy and an inferior end 18a adapted to align generally with the perineal region of the female anatomy. Extending between the superior end 18b and the inferior end 18a of the container 14 are opposing outwardly curved sides 18c that are arranged and configured to generally align along the labium majus of the female anatomy.

It will be appreciated the planar surface 20 and the extra-labia sealing surface 22 substantially conform to the planform of the urine voiding apparatus 10.

Figure 3:
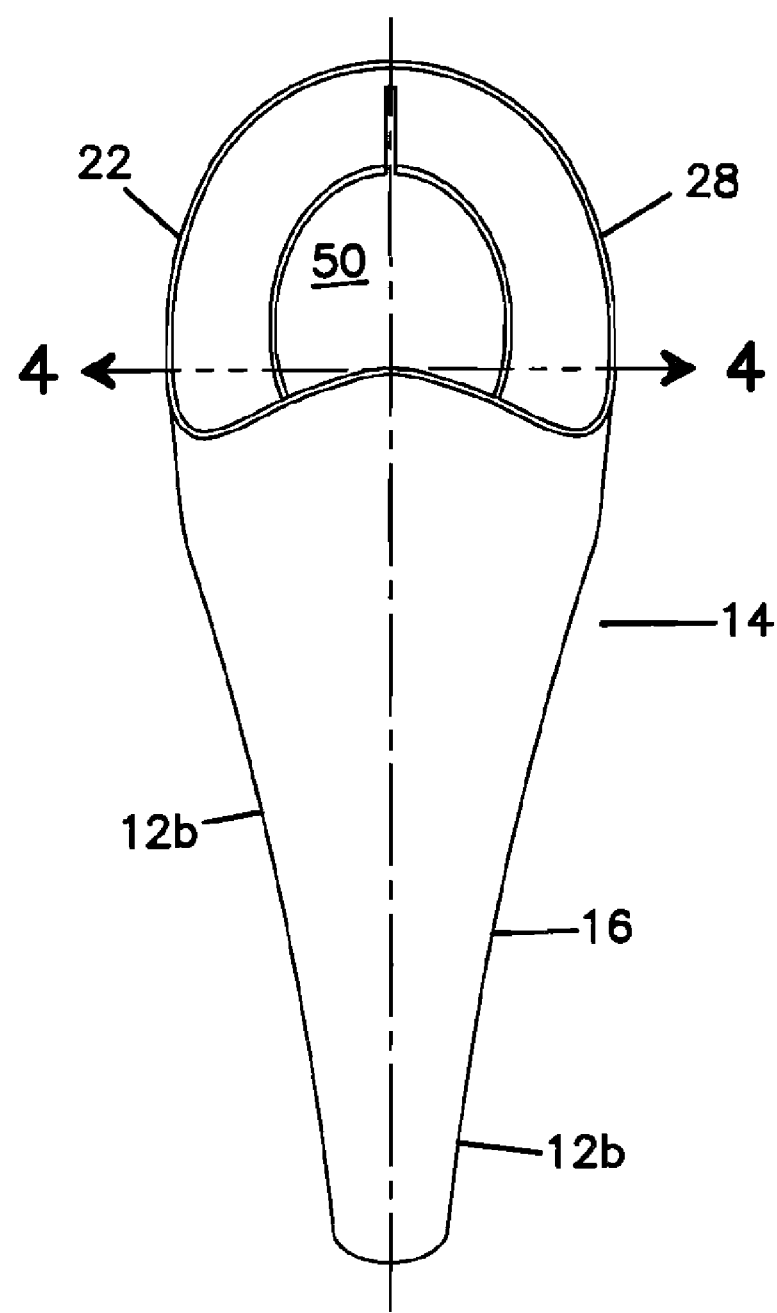
FIG. 3 represents an elevational top perspective view of the urine voiding apparatus of FIG. 1.
Figure 4:
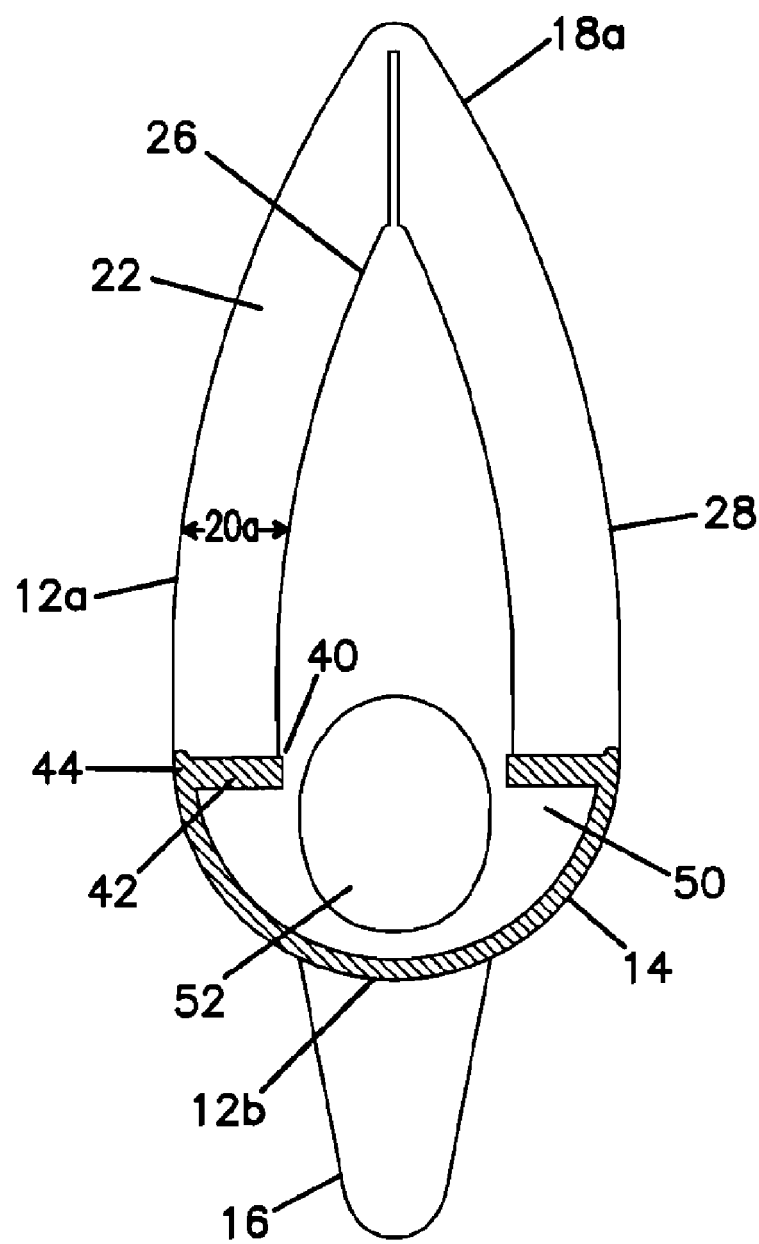
FIG. 4 represents a partial sectional view of the urine voiding apparatus of FIG. 1.

Preferably, the planar surface 20 of the container 14 surrounds the perimeter of the open side 13 at the top 12a of the container 22 and is adapted to face and generally surround a user's vulval region. Optionally, the planar surface 20 resides on a flange or rim 26. As above in FIGS. 1-4, a raised ridge 28, substantially resembling a rib-like structure or protrusion, is preferably disposed proximate the top 12a of the container 14 on the planar surface 20 and about the perimeter of the outer surface of the container 14. The raised ridge 28 is adjacent the pressure sensitive adhesive 22. The raised ridge 28 assists in preventing leakage from the urine voiding apparatus 10 when the apparatus is supported against the periphery of a user's vulval region during use. Preferably, as best shown in FIGS. 3 and 4, the planar surface 20 extends inwardly from the outer surface and perimeter of the container 14. It will be appreciated the planar surface 20 also may be a flange or rim extending outwardly (not shown) from the outer surface and perimeter of the container 14, so as to overhang past the outer surface and perimeter of the container 14. The planar surface 20 includes a width 20a, where the width 20a provides suitable contact area for the optional pressure sensitive adhesive 22 to be affixed to the planar surface 20 and thereby suitably contact a user's vulval region when the urine voiding apparatus 10 is in use. The urine voiding apparatus may also be used without any adhesive.

In one embodiment, the pressure sensitive adhesive 22 of the urine voiding apparatus 10 is a gel-like material affixed to the planar surface 20 of the container 14. Preferably, the pressure sensitive adhesive 22 is directly applied to the planar surface 20 of the container 14. More preferably, the pressure sensitive adhesive is covered with a non-stick backing 24, such as the backing conventionally used on stickers. The backing 24 prevents the pressure sensitive adhesive 22 from adhering to objects when the urine voiding apparatus 10 is not being used. Examples of suitable materials employed for construction of the pressure sensitive adhesive 22 may include but are not limited to 3M Hydrogel and 3M Hydrocolloid 9943. More preferably, the adhesive 22 is a hydrocolloid adhesive, such as Hydrocolloid Adhesive by Avery Dennison MED 2191H. FIGS. 2-4 illustrate the apparatus without the backing 24. It will be appreciated that these materials are merely exemplary as other adhesive materials also may be suitable.

It will be appreciated that other materials may be employed in providing the pressure sensitive adhesive 22. For example, a double-sided adhesive tape (not shown) may be employed that includes a carrier film having opposing sides coated with adhesive. A first side of such an adhesive tape would be affixed to the planar surface 20 of the container 14 such that the adhesive extends completely around the perimeter of the open side 13 of the container 14. A second side of the adhesive tape would be adapted to provide a generally fluid tight primary adhesive seal between the container 14 and a user's external tissue generally surrounding the vulval region.

It is preferred that the pressure sensitive adhesive 22 has a greater bond strength with respect to the container 14 or with respect to a carrier film the pressure sensitive adhesive 22 may reside on than a bond strength with respect to the external tissue surrounding the vulval region. Such a difference in bond strength causes substantially no adhesive residue to remain on the external tissue surrounding the vulval region after the urine voiding apparatus 10 is used. Preferably, the pressure sensitive adhesive 22 is permanently affixed to the planar surface 20 of the container 14 such that the adhesive 22 will not pull away from the container 14 when the voiding apparatus 10 is removed from the vulval region.

When the urine voiding apparatus 10 is placed over the vulval region of the female anatomy, the pressure sensitive adhesive 22 forms a generally fluid tight seal between the container 14 and external tissue generally surrounding the vulval region of a user such as the tissue of the mons Veneris, labium majus and the tissue of the perineum. In operation, while the pressure sensitive adhesive 22 contacts the vulval region so as to press against the vulval region, the pressure sensitive adhesive 22 holds the container 14 to the external tissue the planar surface 20 surrounds to prevent leakage between the urine voiding apparatus 10 and the external tissue of the vulval region. Further, the pressure sensitive adhesive 22 can allow for the urine voiding apparatus to be a hands-free unit when in use. As above, it also will be appreciated an adhesive may not be employed, and a user may simply fit and press the planar surface to the periphery of the vulval region as necessary to manually hold the urine voiding device 10 in place to provide a suitable seal.

As shown in FIG. 4, the optional blocking mechanism 40 includes a wall 44 connected to the container 14 and facing the reservoir 50. The wall 44 is generally disposed proximate the open side 13 of the container 14 about a perimeter of the reservoir 50 and extends a distance inward from the perimeter of the reservoir 50. The wall 44 includes a blocking surface 42 thereon, in which the blocking surface 42 provides a front that counters urine voided from a user's body from escaping through the open side 13 of the container 14 and contacting the user. Particularly, the blocking surface 42 prevents splash back of urine already voided from a user's body that may bounce off or reflect off the sidewalls and boundaries of the inside of the container, thereby at least reducing and substantially eliminating any uncomfortable effects from such conditions.

The wall 44 defines an overlap covering a portion of the reservoir 50 proximate the open side 13. The overlap is arranged and constructed such that the open side 13 and reservoir are not obstructed from receiving urine discharged from a user's body. More preferably, the wall 44 and blocking surface 42 substantially are flat shaped and perpendicular to the direction of flow through the opening 52 and conduit 16.

As shown in FIG. 4, the blocking mechanism 40 may be directly opposite from the planar surface 20, and the blocking mechanism 40 is substantially parallel with the open side 13 and planar surface 20 of the container 14. Preferably, the wall 44 extends to the opening defined by the open side 13. It will be appreciated that the configuration illustrated in FIG. 4 is merely exemplary as other configurations also may be employed.

In operation, the blocking mechanism 40 prevents urine voided from a user's body from escaping through the open side 13 of the container 14 and contacting the user. Additionally, the blocking mechanism 40 can assist the raised ridge 28 in preventing leakage, as urine is blocked from exiting out of the open side 13 at the top 12a of the container 14.

It will be appreciated that the container 14 is preferably compact to facilitate carrying the urine voiding device, for instance, in a purse, daypack, travelbag or the like. It will be appreciated that the container 14 may be constructed of a rigid, semi rigid, or flexible material to further facilitate carrying the urine voiding apparatus 10. Preferably, the material used to produce the container 14 is a light weight material. The container 14 may be manufactured of a plastic, rubber or latex material. More preferably, the container 14 is constructed of a flexible and foldable material so that the urine voiding apparatus 10 may be packaged in a compact size for convenience in handling and transport. Preferably, the urine voiding apparatus may be folded to a dimension of 1.75×3.5× 1.25 inches. The container may be formed from Dow Corning Q7-4750 LSR (Liquid Silicone) or General Electric LIM® (Liquid Injection Molding) 6071. Preferably, the container is formed from 60 durameter silicone. Alternatively, the material used for producing the container may be a thermoplastic elastomer compound such as Dynaflex G6713-0001 by GLS Corp. It will be appreciated that the above materials are exemplary only, as other materials may also be suitable for the manufacture of the container 14. Preferably, the material used for producing the container has material properties that allow the apparatus to spring back to its original form after storage in a folded configuration. This feature may be achieved with a silicone rubber.

It will be appreciated that the volume of the reservoir 50 and the diameter of the conduit 16 can be varied to achieve a desired voiding pressure within the container 14. Further, the length of the conduit 16 may vary, and the conduit 16 may be adapted for attachment to a line (not shown). Additionally, various embodiments of the fluid voiding apparatus 10 can be constructed having pressure sensitive adhesives 22 of different adhesive bond strengths. The adhesive bond strengths will vary depending upon a variety of factors such as skin sensitivity, voiding pressures, the dimensions of the voiding apparatus 10, and the particular application. For example, a stronger adhesive bond strength may be required to provide a total hands-free seal as compared to an adhesive that is used to provide a manually assisted seal.

It will also be appreciated that the urine voiding apparatus 10 can be constructed in various sizes so that the proper apparatus can be chosen for a best fit. It will further be appreciated that the urine voiding apparatuses 10 of different sizes and shapes can be manufactured in different colors corresponding to a particular size so as to color code the urinary voiding apparatuses 10. If an adhesive is used, color coding can also be used to indicate different adhesive bond strengths.

Figure 5:
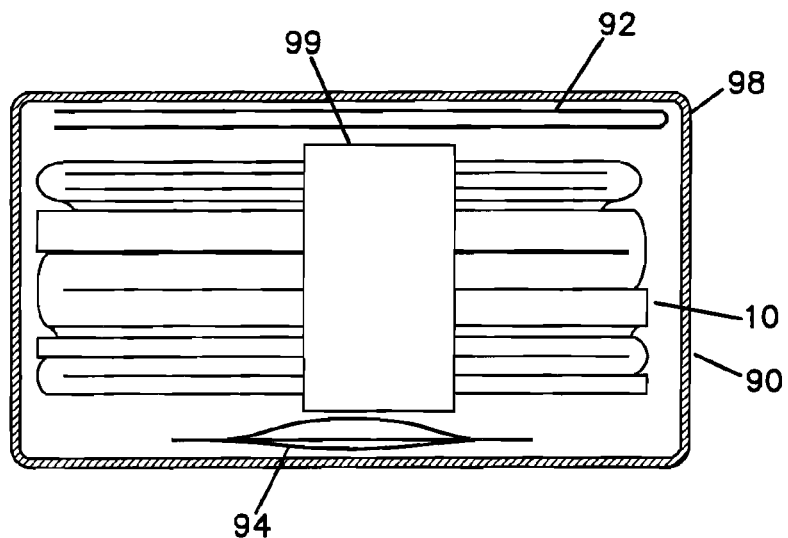
FIG. 5 represents a schematic sectional view of one embodiment of a urine voiding apparatus incorporated in a kit.
Figure 8:
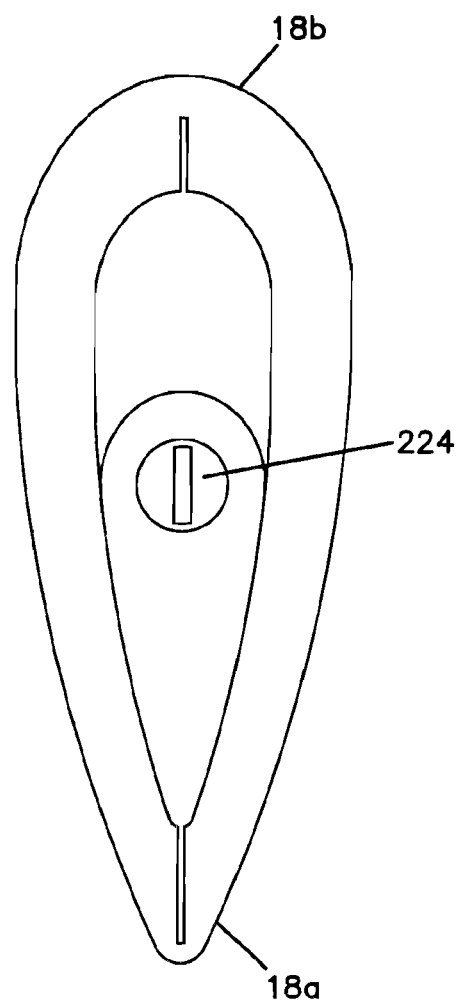
FIG. 8 represents a top view of a urine voiding apparatus.

FIG. 5 shows one example of a urine voiding kit 90 incorporating a urine voiding apparatus 10' in accordance with the principles of the present invention. The features of the urine voiding device 10' include the same features as described above for the urine device 10, and are not further discussed. The kit 90 also includes a packaging container 98. The packaging container 98 may be constructed using well known structures and methods. For example, the packaging container may be "pegable" chipboard box, i.e. a box that can be presented in a store hanging on a peg. The box may also be formed from cardboard or paper cardstock. Preferably, a piece of material 94 adapted for wiping the vulval region after urination is included and packaged along with the urine voiding device 10' in the container 98. The material is preferably a moist antibacterial towelette but could also be a napkin or tissue wipe. For example, a moistened antibacterial towelette containing 0.2% Benzethonium Chloride as the active ingredient may be used. In active ingredients may include Aloe Vera Extract, Apricot Extract, Bezalkonium Chloride, water, and other ingredients. Alternatively, absorbent material may be used. It will be appreciated that the kit 90 may not be resealable and the urine voiding device 10' and kit 90 may both be readily discarded after use. It will also be appreciated that the structure and configuration of the kit 90 may be varied.

In practice, the kit 90 is preferably sized so as to be easily carried, for instance in a purse or the like. As above, the urine voiding apparatus may be folded in a compact size for convenience in handling and transport. Preferably, the urine voiding apparatus is folded to a dimension of 1.75×3.5×1.25 inches. In use, a female removes the urine voiding apparatus 10' from the sealed packaging container 98. The urine voiding apparatus 10' is then placed over the vulval region and the planar surface 20 is pressed toward the body to form a generally fluid tight seal between the planar surface 20 and the external tissue generally surrounding the vulval region. Urine is received in the reservoir 50 of the container 14, and is directed away from the user's body through the opening 52 and the conduit 16.

The user may simply fit and press the planar surface to the periphery of the vulval region as necessary to manually hold the urine voiding device 10' in place and provide a suitable seal. A user can focus attention on directing the urine traveling through the conduit 16 to a particular location, such as a toilet.

After the voiding process is complete, the user removes the urine voiding apparatus 10' from the vulval region and dries the vulval region with the wipe 94. Finally, the wipe 94 and the urine voiding apparatus 10' are placed in the separate bag 92 is employed and adapted for containing the urine voiding apparatus 10' and piece of material 94 after usage. The bag may be sealable for example by a zip-lock mechanism, by tying the bag in a knot, or by other methods known to those skilled in the art. The bag may also be sealed with a twist tie, i.e. a short length of wire encased in a strip of paper, plastic, or foil, designed to be twisted around an item or items as a fastener. It will be appreciated that the urine voiding apparatus 10' and the packaging container 98 also may be discarded immediately after use.

As above, the present invention provides an efficient urine voiding apparatus for use by females which is light weight and compact so that it can be conveniently carried while occupying a minimum amount of space, such as in a purse. Further, the present invention provides a urine voiding apparatus with a blocking mechanism that prevents uncomfortable splash back of urine at the user when the apparatus is being used during urination. The present invention also provides a urine voiding apparatus that is usable while disturbing a minimum amount of garb by the user, and is sanitary and readily disposable after use.

Figure 6:
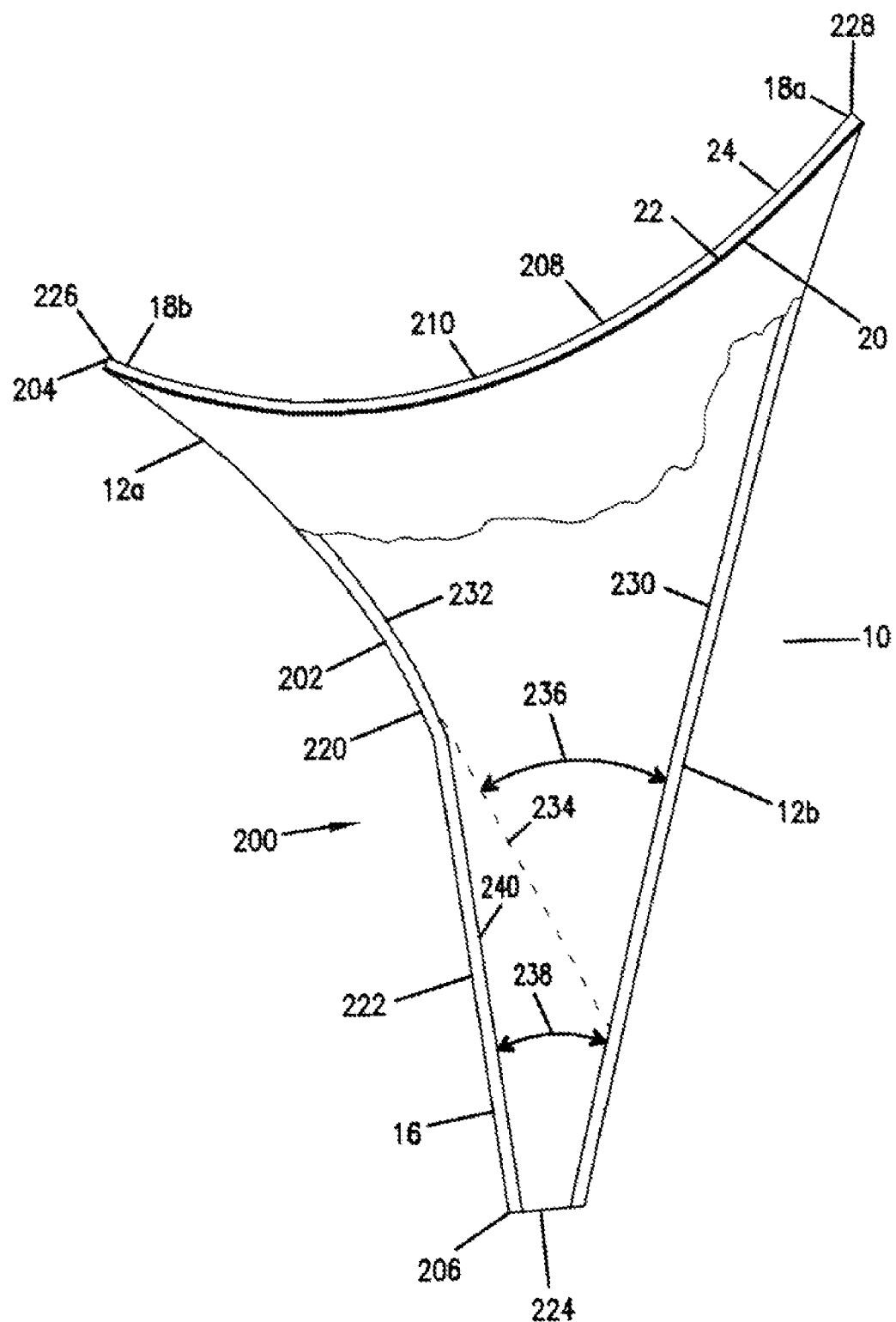
FIG. 6 represents an partially cutaway elevational side plan view of a preferred embodiment of a urine voiding apparatus in accordance with the principles of the present invention.
Figure 7:
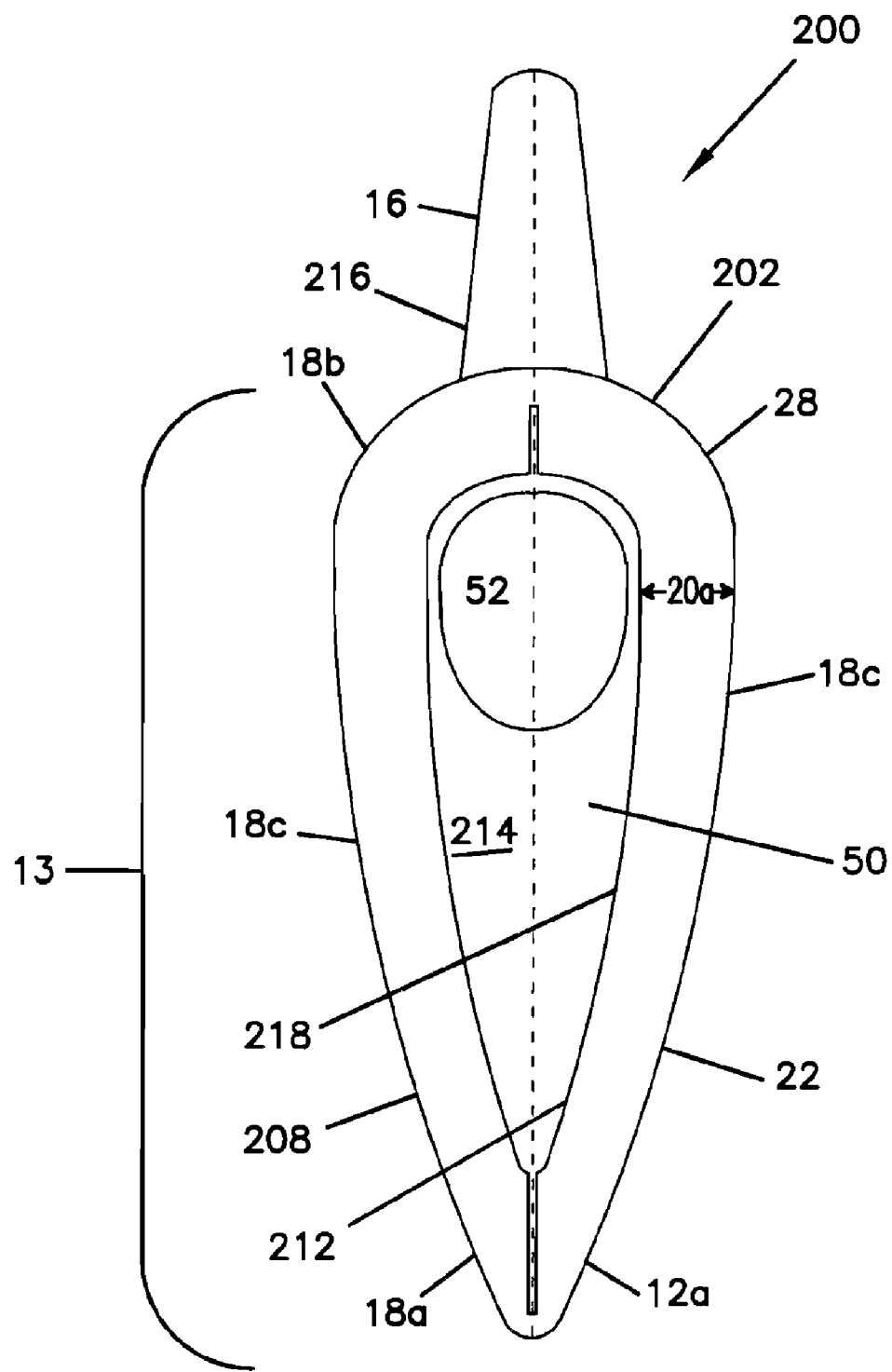
FIG. 7 represents an elevational top plan view of the urine voiding apparatus of FIG. 6.

FIGS. 6 and 7 show a preferred extra-labia urine voiding apparatus 200. The apparatus includes a container 202 having a top 204 and a bottom 206. The top is sized and shaped to cover a vulval region of a female anatomy. An upper surface 208 at the top 204 of the container 202 is arranged to face and generally surround a periphery of the vulval region. The top includes an open side 210 which has an opening 212 for receiving urine into the apparatus 200. The opening 212 is shown in FIG. 7.

The container has interior surfaces 214 and exterior surfaces 216. The interior surfaces define a reservoir 218 on the interior of the apparatus 202. The reservoir is tapered from the opening 212 to a narrower portion 220 lower in the container 202. Below the reservoir, a conduit 222 extends generally downwardly to the bottom of the container. At the end of the conduit is an opening 224 for draining urine from the container 202. Optionally, a pressure sensitive adhesive may be affixed to the upper surface 208 for promoting an adhesive seal between the container and local tissue.

Preferably, the container 202 and conduit 222 are formed from an opaque material so that a user cannot see the flow of urine through the container and conduit. The container and conduit are also preferably formed from a resilient substance, so that the apparatus may be rearranged, i.e., folded, into a compressed configuration for storage without substantial permanent deformation of the apparatus. Depending on the material selected, the apparatus may spring back to its original configuration when restraints such as a box or paper band 99 are removed. Silicone rubber, for example, provides good shape memory to allow the apparatus to return to its original shape when removed from a storage container. In one embodiment the apparatus is folded into a compressed configuration and maintained in that configuration with the restraint such as a piece of paper looped around the apparatus and adhered to itself with an appropriate adhesive.

The apparatus has a front side 226 and a back side 228. The opening 212 is wider at the front side than at the back side.

The interior surface defines a generally linear path 230 that extends from the opening on the top of the container to the opening 224 in the bottom of the container. Preferably the apparatus is symmetric about a plane that passes through the path 230. The interior surfaces of the apparatus also define a front surface 232 at the front side of the apparatus. The front surface defines a front surface axis 234. In the preferred embodiment, the front surface axis 234 and the path 230 form an angle of approximately 50 degrees. The front surface axis can form an angle with the path 230 of between 45 and 55 degrees. Preferably, as shown in FIG. 6, the path 230 extends through both a reservoir and a conduit to promote fluid flow out of the apparatus.

The conduit preferably includes a surface 240 opposed to the path that defines an axis which is offset from the path by an angle 238 of approximately 22 degrees. The generally linear path 230 is preferably between 5½ and 7½ inches long. The path can be six to seven inches in length. The front surface 232 near the opening preferably extends for 2 to 3 inches. The conduit surface 240 also preferably extends for 2 to 3 inches. The above-described surfaces are generally smoothly contoured. The surfaces are not necessarily linear but the overall configuration and orientation of the surfaces operates to promote efficient flow of urine through the apparatus with minimal splash back.

The apparatus is available in a kit as previously described. The bag preferably includes a mechanism for sealing a used apparatus in the bag, such as a zip-lock sealing mechanism, a twist tie or handles for tying the bag. The apparatus may be provided in packaging which combines a plurality of kits. For example the kits may be provided in a box which contains 35 or up to 100 kits or more. The material provided in the kits is preferably material impregnated with anti-bacterial substance. For example an anti-bacterial towelette may be provided in a sealed package within the kit.

With regard to the foregoing description, it is to be understood that changes may be made in detail, especially in matters of the construction materials employed and the shape, size, and arrangement of the parts without departing from the scope of the present invention. It is intended that the specification and depicted embodiment be considered exemplary only, with a true scope and spirit of the invention being indicated by the broad meaning of the following claims.

We claim:

1. An extra-labia urine voiding apparatus comprising:
   a container including a top and a bottom, the top being sized and shaped to externally cover a vulval region of a female anatomy, the container defining a reservoir between the top and the bottom, the top having an opening adapted for receiving urine into the reservoir;
   a blocking mechanism including a wall connected to the container, the wall is generally disposed proximate the opening at the top of the container between a superior end and an inferior end, and the wall extends a distance inward relative to a perimeter of the reservoir,
   the wall includes a blocking surface thereon, in which the blocking surface provides a front that counters urine voided from a user's body from escaping through the opening at the top of the container and contacting the user; and
   a conduit in fluid communication with the reservoir of the container disposed at the bottom of the container, the conduit is configured to guide urine generally downwardly and forwardly toward a lower opening of the conduit for draining urine from the reservoir of the container.

2. The urine voiding apparatus of claim 1, wherein the wall includes a space proximate the superior end and a space proximate the inferior end.

3. The urine voiding apparatus of claim 1, wherein the space proximate the superior end is arranged in a direction from an end of the wall toward the superior end, and the space proximate the inferior end is arranged in a direction from an end of the wall toward the superior end.

4. The urine voiding apparatus of claim 1, wherein the lower opening of the conduit is smaller than a passage through a major portion of the conduit.

5. An extra-labial urine voiding kit comprising:
   a) an extra-labia urine voiding apparatus that includes:
      a container including a top and a bottom, the top being sized and shaped to externally cover a vulval region of a female anatomy, the container defining a reservoir between the top and the bottom, the top having an opening adapted for receiving urine into the reservoir;
      a blocking mechanism including a wall connected to the container, the wall is generally disposed proximate the opening at the top of the container between a superior end and an inferior end, and the wall extends a distance inward relative to a perimeter of the reservoir,
      the wall includes a blocking surface thereon, in which the blocking surface provides a front that counters urine voided from a user's body from escaping through the opening at the top of the container and contacting the user; and
      a conduit in fluid communication with the reservoir of the container disposed at the bottom of the container, the conduit is configured to guide urine generally downwardly and forwardly toward a lower opening of the conduit for draining urine from the reservoir of the container;
   b) a piece of absorbent material adapted for wiping the vulval region;
   c) a bag contained within the packaging structure, the bag being adapted for containing the urine voiding apparatus and piece of absorbent material after usage; and
   d) a packaging structure that contains the urine voiding apparatus, the piece of absorbent material, and the bag.

* * * * *